United States Patent
Simons et al.

(10) Patent No.: US 9,119,945 B2
(45) Date of Patent: Sep. 1, 2015

(54) DEVICE FOR APPLYING A MICRONEEDLE ARRAY

(75) Inventors: John K. Simons, Maplewood, MN (US); Franklyn L. Frederickson, Duluth, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 467 days.

(21) Appl. No.: 12/296,590

(22) PCT Filed: Apr. 20, 2007

(86) PCT No.: PCT/US2007/067063
§ 371 (c)(1),
(2), (4) Date: Oct. 9, 2008

(87) PCT Pub. No.: WO2007/124411
PCT Pub. Date: Nov. 1, 2007

(65) Prior Publication Data
US 2009/0198189 A1    Aug. 6, 2009

Related U.S. Application Data

(60) Provisional application No. 60/793,564, filed on Apr. 20, 2006.

(51) Int. Cl.
*A61M 5/00* (2006.01)
*A61M 37/00* (2006.01)

(52) U.S. Cl.
CPC ... *A61M 37/0015* (2013.01); *A61M 2037/0023* (2013.01); *A61M 2037/0061* (2013.01)

(58) Field of Classification Search
CPC .............. A61M 37/0015; A61M 2037/0023; A61M 2037/0061
USPC .................. 604/173, 20, 21, 22, 191
See application file for complete search history.

(56) References Cited

U.S. PATENT DOCUMENTS

| | | | |
|---|---|---|---|
| 3,034,507 A | 5/1962 | McConnell et al. |
| 3,072,122 A | 1/1963 | Rosenthal |

(Continued)

FOREIGN PATENT DOCUMENTS

| | | |
|---|---|---|
| AU | 2005200910 B2 | 3/2005 |
| EP | 0 407 063 | 1/1991 |

(Continued)

OTHER PUBLICATIONS

ASTM D1238, "Standard Test Method for Melt Flow Rates of Thermoplastics by extrusion Plastometer".

(Continued)

*Primary Examiner* — Kami A Bosworth
*Assistant Examiner* — William Carpenter
(74) *Attorney, Agent, or Firm* — Colene H. Blank

(57) ABSTRACT

A device (100) for applying a microneedle array to a skin surface. The device comprises a base (120) defining a skin contacting plane, an array component having a skin facing side comprising a microneedle array, and at least one connecting member (140) having a first portion affixed through a first hinge (142) to the base and a second portion affixed to the array component. The connecting member has a first equilibrium position with the microneedle array in a recessed position within the device and a second equilibrium position with the microneedle array positioned so as to be able to contact a skin surface.

21 Claims, 10 Drawing Sheets

(56) References Cited

U.S. PATENT DOCUMENTS

| | | | |
|---|---|---|---|
| 3,123,212 A | 3/1964 | Taylor et al. | |
| 3,136,314 A | 6/1964 | Kravitz | |
| RE25,637 E | 9/1964 | Kravitz et al. | |
| 3,221,740 A | 12/1965 | Rosenthal | |
| 3,246,647 A | 4/1966 | Taylor et al. | |
| 3,322,121 A | 5/1967 | Banker | |
| 3,466,131 A | 9/1969 | Arcudi | |
| 3,510,933 A | 5/1970 | Taylor et al. | |
| 3,512,520 A | 5/1970 | Cowan | |
| 3,596,660 A | 8/1971 | Melone | |
| 3,675,766 A | 7/1972 | Rosenthal | |
| 3,678,150 A | 7/1972 | Szumski et al. | |
| 3,688,764 A | 9/1972 | Reed | |
| 3,905,371 A | 9/1975 | Stickl et al. | |
| 3,964,482 A | 6/1976 | Gerstel et al. | |
| 4,109,655 A | 8/1978 | Chacornac | |
| 4,237,906 A | 12/1980 | Havstad et al. | |
| 4,304,241 A | 12/1981 | Brennan | |
| 4,360,016 A | 11/1982 | Sarrine | |
| 4,435,926 A | 3/1984 | Struben | |
| 4,474,751 A | 10/1984 | Haslam et al. | |
| 4,503,856 A | 3/1985 | Cornell et al. | |
| 4,517,978 A | 5/1985 | Levin et al. | |
| 4,637,403 A | 1/1987 | Garcia et al. | |
| 4,858,607 A | 8/1989 | Jordan et al. | |
| 4,869,249 A | 9/1989 | Crossman et al. | |
| 4,920,977 A | 5/1990 | Haynes | |
| 4,924,879 A | 5/1990 | O'Brien | |
| 5,192,535 A | 3/1993 | Davis et al. | |
| 5,250,023 A | 10/1993 | Lee et al. | |
| 5,318,584 A | 6/1994 | Lange et al. | |
| 5,340,572 A | 8/1994 | Patel et al. | |
| 5,366,469 A | 11/1994 | Steg et al. | |
| 5,368,047 A | 11/1994 | Suzuki et al. | |
| 5,402,798 A | 4/1995 | Swierczek et al. | |
| 5,487,726 A | 1/1996 | Rabenau et al. | |
| 5,611,806 A | 3/1997 | Jang | |
| 5,879,326 A | 3/1999 | Godshall et al. | |
| 5,983,136 A | 11/1999 | Kamen | |
| 6,050,988 A | 4/2000 | Zuck | |
| 6,091,975 A | 7/2000 | Daddona et al. | |
| 6,132,755 A | 10/2000 | Eicher et al. | |
| 6,219,574 B1* | 4/2001 | Cormier et al. | 604/20 |
| 6,256,533 B1 | 7/2001 | Yuzhakov et al. | |
| 6,293,925 B1 | 9/2001 | Safabash et al. | |
| 6,312,612 B1 | 11/2001 | Sherman et al. | |
| 6,322,808 B1 | 11/2001 | Trautman et al. | |
| 6,334,856 B1 | 1/2002 | Allen et al. | |
| 6,379,324 B1 | 4/2002 | Gartstein et al. | |
| 6,440,096 B1 | 8/2002 | Lastovich et al. | |
| 6,454,755 B1 | 9/2002 | Godshall | |
| 6,503,231 B1 | 1/2003 | Prausnitz et al. | |
| 6,532,386 B2 | 3/2003 | Sun et al. | |
| 6,537,242 B1* | 3/2003 | Palmer | 604/22 |
| 6,589,202 B1 | 7/2003 | Powell | |
| 6,591,124 B2 | 7/2003 | Sherman et al. | |
| 6,595,947 B1 | 7/2003 | Mikszta et al. | |
| 6,603,998 B1 | 8/2003 | King et al. | |
| 6,611,707 B1 | 8/2003 | Prausnitz et al. | |
| 6,623,457 B1 | 9/2003 | Rosenberg | |
| 6,656,147 B1* | 12/2003 | Gertsek et al. | 604/28 |
| 6,713,291 B2 | 3/2004 | King et al. | |
| 6,743,211 B1* | 6/2004 | Prausnitz et al. | 604/239 |
| 6,780,171 B2* | 8/2004 | Gabel et al. | 604/181 |
| 6,797,276 B1 | 9/2004 | Glenn et al. | |
| 6,830,562 B2 | 12/2004 | Mogensen et al. | |
| 6,855,131 B2 | 2/2005 | Trautman et al. | |
| 6,881,203 B2 | 4/2005 | Delmore et al. | |
| 6,881,538 B1 | 4/2005 | Haddad et al. | |
| 6,890,319 B1 | 5/2005 | Crocker | |
| 6,908,453 B2 | 6/2005 | Fleming et al. | |
| 6,931,277 B1 | 8/2005 | Yuzhakov et al. | |
| 7,004,928 B2 | 2/2006 | Aceti et al. | |
| 7,087,035 B2* | 8/2006 | Trautman et al. | 604/22 |
| 7,250,037 B2 | 7/2007 | Shermer et al. | |
| 7,419,481 B2 | 9/2008 | Trautman et al. | |
| 7,455,654 B2* | 11/2008 | Cormier et al. | 604/46 |
| 7,798,987 B2 | 9/2010 | Trautman et al. | |
| 2001/0044606 A1 | 11/2001 | Inkpen et al. | |
| 2002/0032415 A1 | 3/2002 | Trautman et al. | |
| 2002/0082543 A1 | 6/2002 | Park et al. | |
| 2002/0087182 A1 | 7/2002 | Trautman et al. | |
| 2002/0091357 A1 | 7/2002 | Trautman et al. | |
| 2002/0095134 A1 | 7/2002 | Pettis et al. | |
| 2002/0111600 A1 | 8/2002 | Cormier et al. | |
| 2002/0123675 A1 | 9/2002 | Trautman et al. | |
| 2002/0128599 A1 | 9/2002 | Cormier et al. | |
| 2002/0138049 A1 | 9/2002 | Allen et al. | |
| 2002/0169416 A1 | 11/2002 | Gonnelli et al. | |
| 2002/0177839 A1 | 11/2002 | Cormier et al. | |
| 2002/0177858 A1 | 11/2002 | Sherman et al. | |
| 2002/0188245 A1 | 12/2002 | Martin et al. | |
| 2002/0193729 A1 | 12/2002 | Cormier et al. | |
| 2002/0198509 A1 | 12/2002 | Mikszta et al. | |
| 2003/0045837 A1 | 3/2003 | Delmore et al. | |
| 2003/0050602 A1 | 3/2003 | Pettis et al. | |
| 2003/0083641 A1 | 5/2003 | Angel et al. | |
| 2003/0083645 A1* | 5/2003 | Angel et al. | 604/890.1 |
| 2003/0135158 A1 | 7/2003 | Gonnelli | |
| 2003/0135161 A1* | 7/2003 | Fleming et al. | 604/173 |
| 2003/0161869 A1 | 8/2003 | Hatanaka et al. | |
| 2003/0181863 A1 | 9/2003 | Ackley et al. | |
| 2003/0199811 A1* | 10/2003 | Sage et al. | 604/46 |
| 2003/0199812 A1* | 10/2003 | Rosenberg | 604/47 |
| 2003/0208167 A1 | 11/2003 | Prausnitz et al. | |
| 2004/0049150 A1 | 3/2004 | Dalton et al. | |
| 2004/0077994 A1 | 4/2004 | Lastovich et al. | |
| 2004/0138612 A1 | 7/2004 | Shermer et al. | |
| 2004/0176732 A1 | 9/2004 | Frazier et al. | |
| 2004/0181203 A1 | 9/2004 | Cormier et al. | |
| 2005/0025778 A1 | 2/2005 | Cormier et al. | |
| 2005/0027242 A1 | 2/2005 | Gabel et al. | |
| 2005/0065463 A1 | 3/2005 | Tobinaga et al. | |
| 2005/0065466 A1 | 3/2005 | Vedrine | |
| 2005/0065472 A1 | 3/2005 | Cindrich et al. | |
| 2005/0096586 A1 | 5/2005 | Trautman et al. | |
| 2005/0106226 A1 | 5/2005 | Cormier et al. | |
| 2005/0137525 A1 | 6/2005 | Wang et al. | |
| 2005/0228313 A1 | 10/2005 | Kaler et al. | |
| 2005/0261631 A1 | 11/2005 | Clarke et al. | |
| 2007/0021716 A1* | 1/2007 | Hansen | 604/68 |
| 2007/0073220 A1 | 3/2007 | Bunce | |
| 2007/0161964 A1 | 7/2007 | Yuzhakov | |
| 2008/0051699 A1 | 2/2008 | Choi et al. | |
| 2008/0088066 A1 | 4/2008 | Ferguson et al. | |
| 2008/0114298 A1* | 5/2008 | Cantor et al. | 604/117 |
| 2008/0195035 A1 | 8/2008 | Frederickson et al. | |
| 2009/0198189 A1 | 8/2009 | Simons et al. | |
| 2010/0222743 A1 | 9/2010 | Frederickson et al. | |
| 2012/0109066 A1 | 5/2012 | Chase et al. | |

FOREIGN PATENT DOCUMENTS

| | | |
|---|---|---|
| GB | 1080986 | 8/1967 |
| GB | 2 064 329 | 6/1981 |
| GB | 2 221 394 | 2/1990 |
| JP | 6-22941 | 2/1994 |
| JP | 2002-504904 | 2/2002 |
| JP | 2003-321350 | 11/2003 |
| WO | WO 96/10630 | 4/1996 |
| WO | WO 98/55109 | 12/1998 |
| WO | WO 00/74766 | 12/2000 |
| WO | WO 01/36037 | 5/2001 |
| WO | WO 01/93931 | 12/2001 |
| WO | WO 04/000389 | 12/2003 |
| WO | WO 2004/009172 | 1/2004 |
| WO | WO 2005/051455 | 6/2005 |
| WO | WO 2005/051476 | 6/2005 |
| WO | WO 2005/058393 | 6/2005 |
| WO | WO 2005/065765 | 7/2005 |
| WO | WO 2005/082596 | 9/2005 |
| WO | WO 2005/123173 | 12/2005 |
| WO | WO 2006/055795 | 5/2006 |
| WO | WO 2006/055802 | 5/2006 |

(56) References Cited

FOREIGN PATENT DOCUMENTS

| WO | WO 2006055795 A1 * | 5/2006 | ............ A61M 37/00 |
|---|---|---|---|
| WO | WO 2006055802 A1 * | 5/2006 | ............ A61M 37/00 |
| WO | WO 2007/002521 | 1/2007 | |
| WO | WO 2007/002523 | 1/2007 | |
| WO | WO 2011/014514 | 2/2011 | |

OTHER PUBLICATIONS

ASTM D638, "Standard Test Method for Tensile Properties of Plastics".

ASTM D256, "Standard Test Methods for Determining the Izod Pendulum Impact Resistance of Plastics".

Daddona, P.E.; "Recent advances in peptide, protein and macromolecule drug delivery"; Current Opinion in Drug Discovery & Development; vol. 2, No. 2; 1999; pp. 168-171.

Kaushik, S. et al.; "Lack of Pain Associated with Microfabricated Microneedles"; Anesth Analg.; vol. 92; 2001; pp. 502-504.

Henry, S. et al.; "Microfabricated Microneedles: A Novel Approach to Transdermal Drug Delivery"; Journal of Pharmaceutical Sciences; vol. 87, No. 8, 1998; pp. 922-925.

Mcallister, D. et al.; "Microfabricated Microneedles for Gene and Drug Delivery"; Annu. Rev. Biomed. Eng.; vol. 02; 2000; pp. 289-313.

Mcallister, D. et al.; "Solid and Hollow Microneedles for Transdermal Protein Delivery"; Proceed. In'tl. Symp. Control. Rel. Bioact. Mater.; vol. 26; 1999; pp. 192-193.

* cited by examiner

DEVICE FOR APPLYING A MICRONEEDLE ARRAY

CROSS REFERENCE TO RELATED APPLICATIONS

This application is a national stage filing under 35 U.S.C. 371 of PCT/US2007/067063, filed Apr. 20, 2007, which claims priority to U.S. Provisional Application No. 60/793,564, filed Apr. 20, 2006, the disclosure of which is incorporated by reference in its/their entirety herein.

FIELD

The present invention relates to devices for applying a microneedle array to a mammal. The present method also relates to methods of applying a microneedle array to a mammal.

BACKGROUND

Only a limited number of molecules with demonstrated therapeutic value can be transported through the skin via unassisted or passive transdermal drug delivery. The main barrier to transport of molecules through the skin is the stratum corneum (the outermost layer of the skin).

Devices including arrays of relatively small structures, sometimes referred to as microneedles or micro-pins, have been disclosed for use in connection with the delivery of therapeutic agents and other substances through the skin and other surfaces. The devices are typically pressed against the skin in an effort to pierce the stratum corneum such that the therapeutic agents and other substances can pass through that layer and into the tissues below.

Issues related to applying microneedles include the ability to effectively insert the needles to a desired depth in the skin and the ability to protect the delicate microneedles prior to application to the skin.

SUMMARY OF THE INVENTION

In one embodiment, the present invention is a device for applying a microneedle array to a skin surface. The device comprises a base defining a skin contacting plane, an array component having a skin facing side comprising a microneedle array, and at least one connecting member having a first portion affixed through a first hinge to the base and a second portion affixed to the array component. The connecting member has a first equilibrium position with the microneedle array in a recessed position within the device and a second equilibrium position with the microneedle array positioned so as to be able to contact a skin surface.

The present invention also comprises methods of applying such devices to a skin surface and applying a force to the array component sufficient to move the connecting member to its second equilibrium position.

In another embodiment, the present invention is a method of applying a microneedle array to a skin surface. A device is provided having a first equilibrium position wherein a microneedle array is in a recessed position within the device. The device is placed on a skin surface. A mechanical applicator is then brought into contact with the device and a drive mechanism of the mechanical applicator is aligned with the microneedle array. Force is applied via the drive mechanism to the microneedle array sufficient to move the microneedle array into contact with the skin surface. The mechanical applicator is then removed from contact with the device.

As used herein, certain terms will be understood to have the meaning set forth below:

"Array" refers to the medical devices described herein that include one or more structures capable of piercing the stratum corneum to facilitate the transdermal delivery of therapeutic agents or the sampling of fluids through or to the skin.

"Microstructure," "microneedle" or "microarray" refers to the specific microscopic structures associated with the array that are capable of piercing the stratum corneum to facilitate the transdermal delivery of therapeutic agents or the sampling of fluids through the skin. By way of example, microstructures can include needle or needle-like structures as well as other structures capable of piercing the stratum corneum.

The features and advantages of the present invention will be understood upon consideration of the detailed description of the preferred embodiment as well as the appended claims. These and other features and advantages of the invention may be described below in connection with various illustrative embodiments of the invention. The above summary of the present invention is not intended to describe each disclosed embodiment or every implementation of the present invention. The Figures and the detailed description which follow more particularly exemplify illustrative embodiments.

BRIEF DESCRIPTION OF THE DRAWINGS

Preferred embodiments of the invention will now be described in greater detail below with reference to the attached drawings, wherein.

While the above-identified drawing figures set forth several embodiments of the invention, other embodiments are

DETAILED DESCRIPTION

Figure 1:
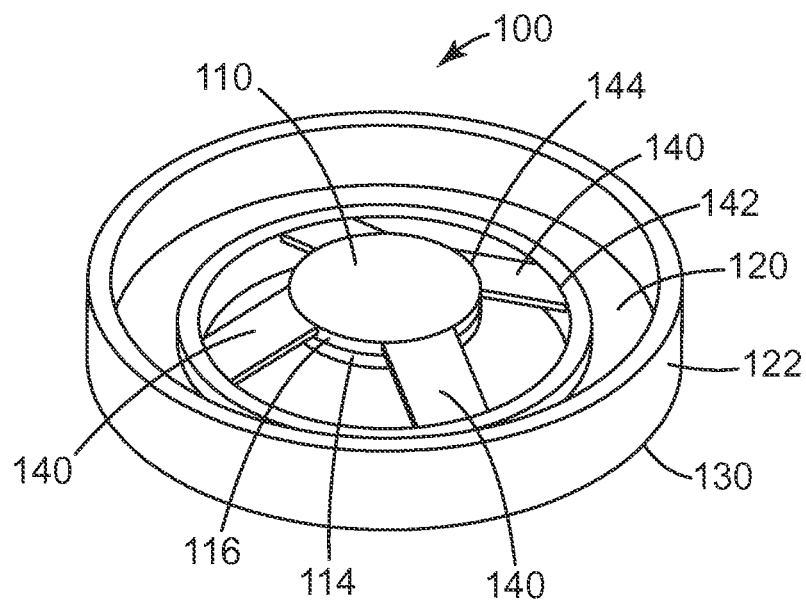
FIG. 1 is a perspective view of the skin distal side of a device for applying a microneedle array to a skin surface.
Figure 2:
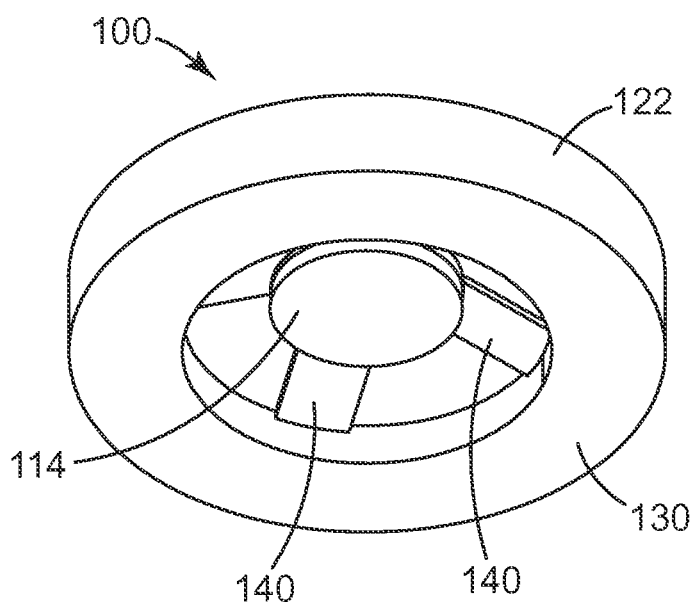
FIG. 2 is a perspective view of the skin facing side of a device for applying a microneedle array to a skin surface.
Figure 14:
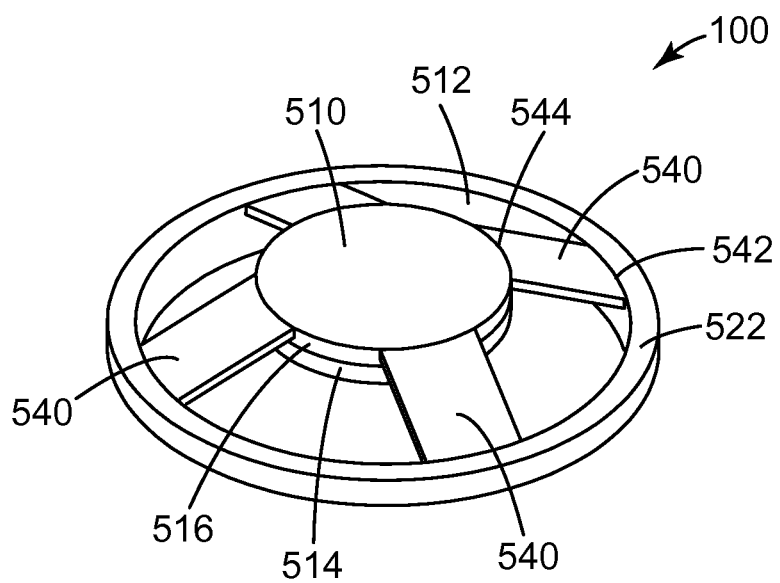
FIG. 14 is a perspective view of the skin distal side of a device showing connecting members attached directly to an outer ring.

One embodiment of the microneedle application device 100 is shown in FIGS. 1 and 2. The skin distal side of the device 100 is shown in FIG. 1 and the skin facing, or proximal, side of the device is shown in FIG. 2. The application device 100 comprises a base 120 affixed to a first portion of four connecting members 140 (only 3 are visible) through a first hinge 142. A second portion of the connecting members 140 is affixed to an array component 110 through a second hinge 144. The array component 110 comprises a backing plate 116 and a microneedle array 114. The skin facing side of the microneedle array, which comprises one or more microneedles (not shown), is more clearly shown in FIG. 2. The connecting members 140 are shown in a first equilibrium position with the array 114 in a recessed position within the device 100. The base 120 comprises a skin-facing, or skin-proximal, side covered with a pressure-sensitive skin adhesive layer 130. The base also comprises an outer ring 122 which can serve a variety of functions, such as lending stiffness and ease of handling to the entire device 100. The outer ring 122 is shown as cylindrical, but can be any shape. As shown, the outer ring 122 extends above the array component 110 on the skin distal side of the device and can provide protection against premature engagement of the array component 110. FIG. 14 shows another embodiment of the microneedle application device 100. In this embodiment, device 100 comprises an outer ring 522 affixed to a first portion of four connecting members 540 through a first hinge 542. A second portion of the connecting members 540 is affixed to an array component 510 through a second hinge 544. The base 120 also defines a skin-contacting plane that, as shown, coincides with the skin-facing side of the pressure-sensitive skin adhesive 130 and extends across the opening in the center of the device. In addition, the skin adhesive layer 130 may be adhered to an optional, removable covering member (not shown), such as a foil and/or plastic film, that can provide protection to the device during storage. The covering member will then be removed and discarded prior to use.

Figure 3:
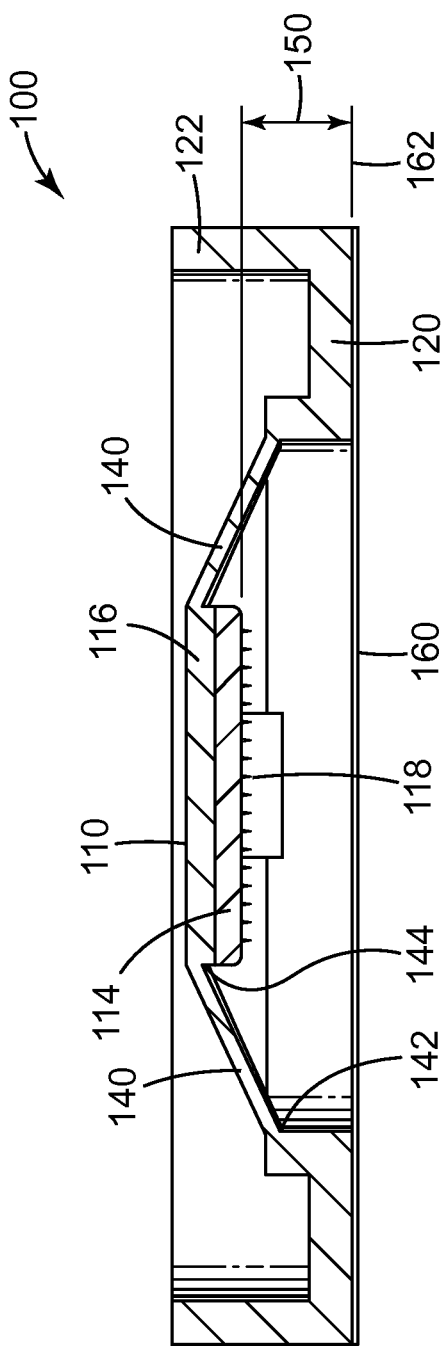
FIG. 3 is a schematic cross-section of a device in a first equilibrium position.
Figure 4:
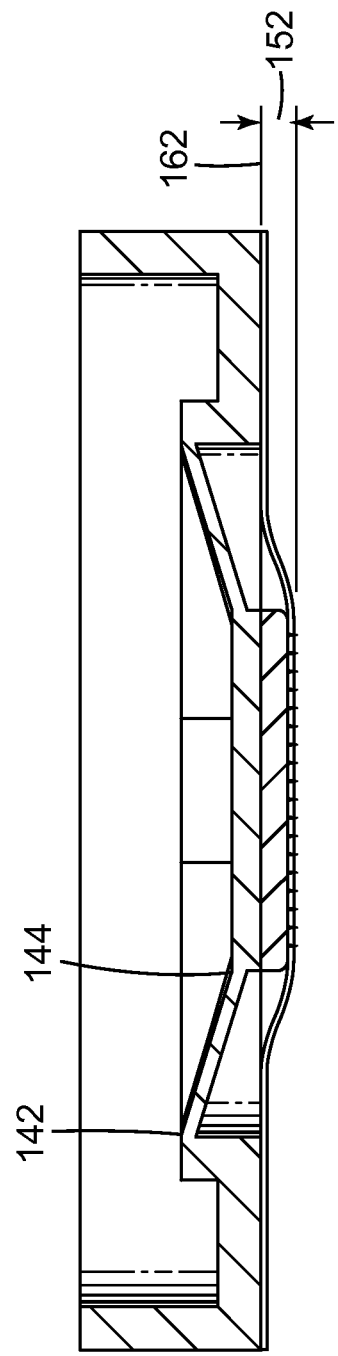
FIG. 4 is a schematic cross-section of a device in a second equilibrium position.

As shown in FIGS. 3 and 4, the connecting members 140 of the device 100 have two equilibrium positions. A first equilibrium position is shown in FIG. 3 where the array component 110 and array 114 are in a recessed position within the device 100. The recessed position allows the device 100 to be placed against a skin surface 160 while preventing the microneedles 118 from prematurely contacting the skin surface 160. The initial position of the microneedle array 114 may be characterized by a setback distance 150, that is, the distance between the skin-contacting plane 162 and the microneedle array 114. Pressure can then be applied to the array component 110 which causes the connecting members 140 to rotate about first and second hinges 142, 144 and thereby moves the connecting members 140 to a second equilibrium position. The hinge can be any of a variety of shapes and structures that allow for the movement or flexure of the connecting member(s) from the first equilibrium position to the second equilibrium position. The array component 110 and microneedle array 114 contact the skin surface 160 in the second equilibrium position, thus allowing the microneedles 118 to penetrate the skin surface. As shown, the microneedle array 114 extends beyond the skin contacting plane 162 by a distance 152. Although not wishing to be bound by theory, it is believed that pressing the microneedle array 114 a small distance beyond the skin-contacting plane 162 and into the skin allows for better retention of the microneedles 118 within the skin.

In one embodiment, the microneedle array 114 may be releasably attached to the backing plate 116. In addition, a portion of the skin-facing side of the array may be covered with a pressure-sensitive adhesive. After application to the skin (as shown in FIG. 4), the base 120, connecting member 140, and backing plate 116 can then be removed from the skin leaving the microneedle array 114 in place. In another aspect, the microneedle array 114 could comprise an adhesive patch releasably attached to the backing plate 116. Such an adhesive patch with a microneedle array could then be applied and left in place after removal of the remainder of the device as described above.

Figure 5:
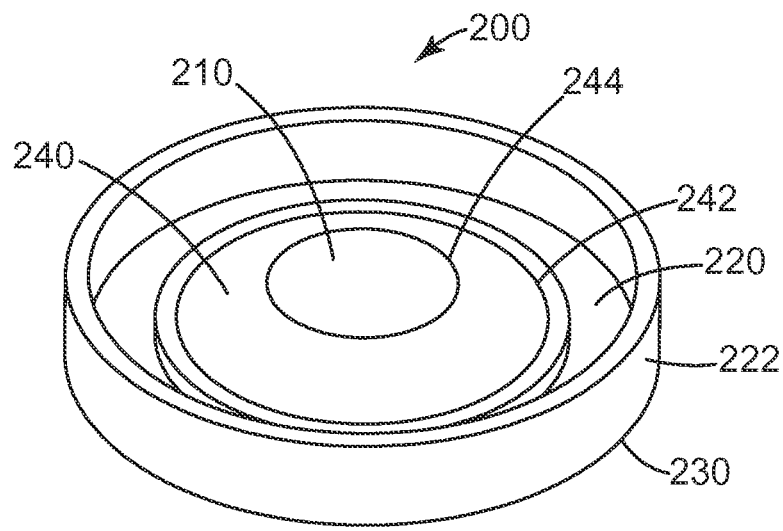
FIG. 5 is a perspective view of the skin distal side of a device for applying a microneedle array to a skin surface.

At least one connecting member connects the base and array component. In one embodiment, a single, flexible connecting member is employed, as shown in FIG. 5. A first portion of the connecting member 240 (i.e., the outer edge of the connecting member 240) is affixed to the base 220 through a first hinge 242 that encircles the connecting member 240. A second portion of the connecting member 240 is affixed to an array component 210 through a second hinge 244 that encircles the array component 210. Other features of the device, such as base 220, outer ring 222, and pressure-sensitive skin adhesive layer 230 are as described in the embodiment shown in FIGS. 1 and 2. In other embodiments, a plurality of connecting members may be used. Four equally spaced connecting members are shown in FIGS. 1 and 2, however two, three, or more than four connecting members may also be used. In one embodiment, multiple connecting members are symmetrically spaced around the array component. FIG. 14 shows another embodiment, wherein the connecting member(s) 540 may be affixed to the outer ring 522.

Although the array may be held in any orientation, it will typically be aligned substantially parallel to the skin contacting plane in both the first and second equilibrium positions. Such an orientation is generally desirable, as the microneedles will often be aligned so as to be perpendicular to the skin surface. Parallel alignment of the array thus allows for the microneedles to be pressed straight downward into the skin, thus minimizing the chance of bending the microneedles and allowing for reproducible penetration to a desired depth in the skin. In one embodiment, the array will also remain substantially parallel to the skin contacting plane when moving from the first equilibrium position to the second equilibrium position. Such an orientation between the equilibrium positions may be desirable, since the microneedles may contact the skin surface prior to the device reaching its second equilibrium position. By substantially parallel, it should be understood that the skin is a biological surface and as such has some natural roughness and irregularity. Thus variations in alignment of the array with respect to parallel having a magnitude similar to that of the natural roughness of a skin surface are considered to be substantially parallel.

Figure 15:
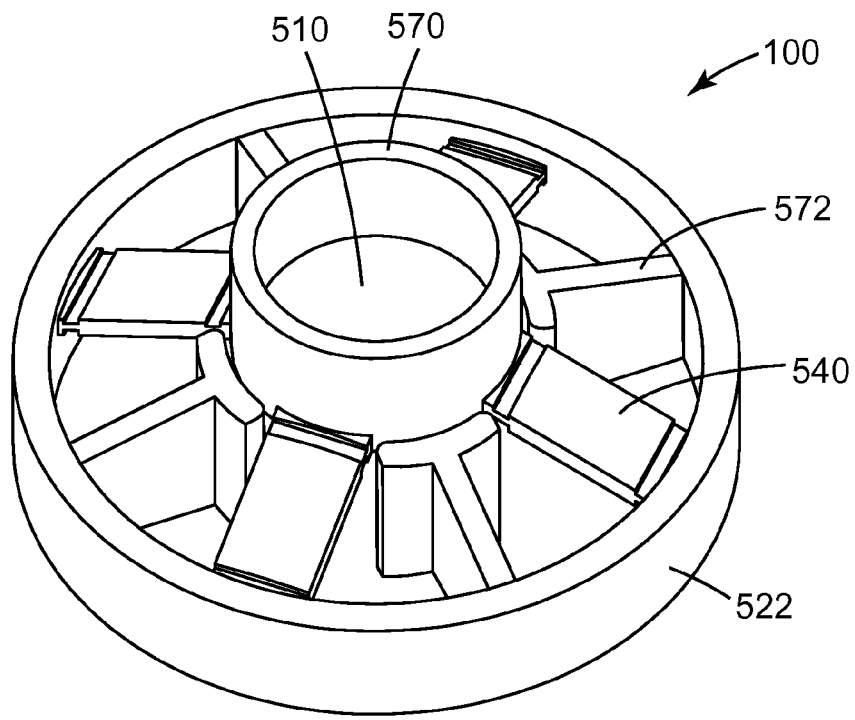
FIG. 15 is a perspective view of the skin distal side of a device showing internal guides.
Figure 16:
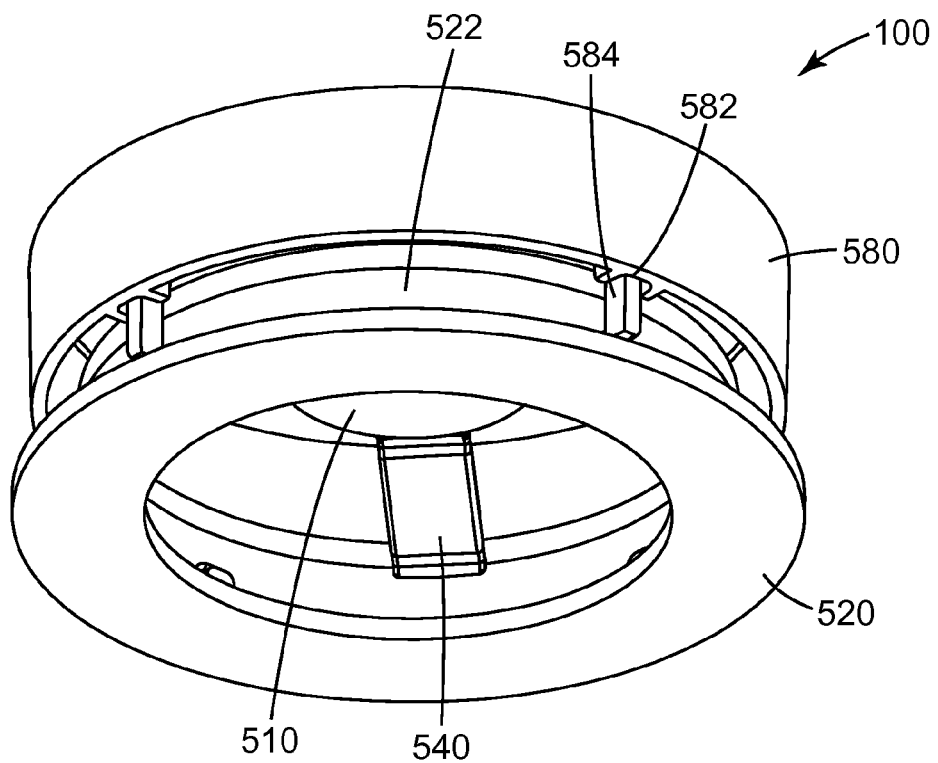
FIG. 16 is a perspective view of the skin facing side of a device showing an external guide.

In another embodiment, internal or external guides may be used to maintain the array's substantially parallel position to the skin contacting plane. FIG. 15 shows a device 100 comprising an outer ring 522 and four connecting members 540. Also affixed to the outer ring 522 are four internal guides 572. The internal guides 572 are affixed to the outer ring 522 and extend radially inward towards the array cylinder 570 with the inward end abutting the array cylinder 570. The array cylinder 570 is shown as a cylindrical ring, but may be of any shape. The array cylinder 570 is affixed to the skin distal surface of the array component 510 and is preferably of a height at least the same as the inner surface of the outer ring. Upon actuation the exterior surface of the array cylinder 570 moves along the internal guides 572 to maintain the substantially parallel orientation of the array 510. External guides are shown in FIG. 16, which shows a device 100 comprising a base 520, connecting members 540 and an array component 510. In this embodiment the base is slightly extended radially outward from the outer ring 522. Outer ring 522 has one or more protrusions 584 on the exterior surface. An array cap 580 is placed over the array 510 and connecting members 540. Upon actuation the array cap 580 comes down over the protrusions 584 on outer ring 522 to the base 520. The array cap 580 has an internal diameter that is at least as wide as the outer diameter of the outer ring 522. The array cap 580 may optionally comprise one or more channels 582 that correspond to the one or more protrusions 584 along the exterior surface of the outer ring 522 thus decreasing any potential rotational movement.

Figure 13:
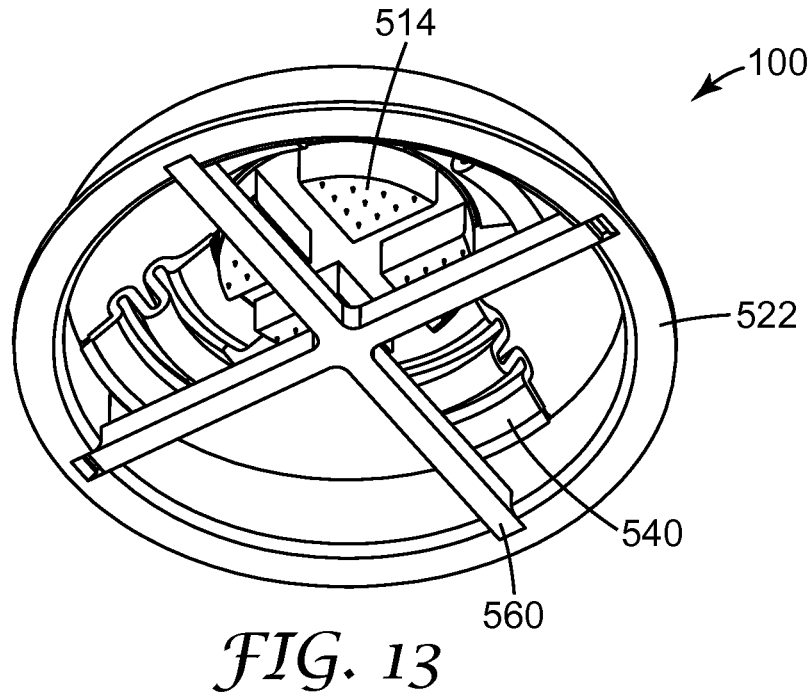
FIG. 13 is a perspective view of the skin facing side of a device showing two cross bars.
Figure 17:
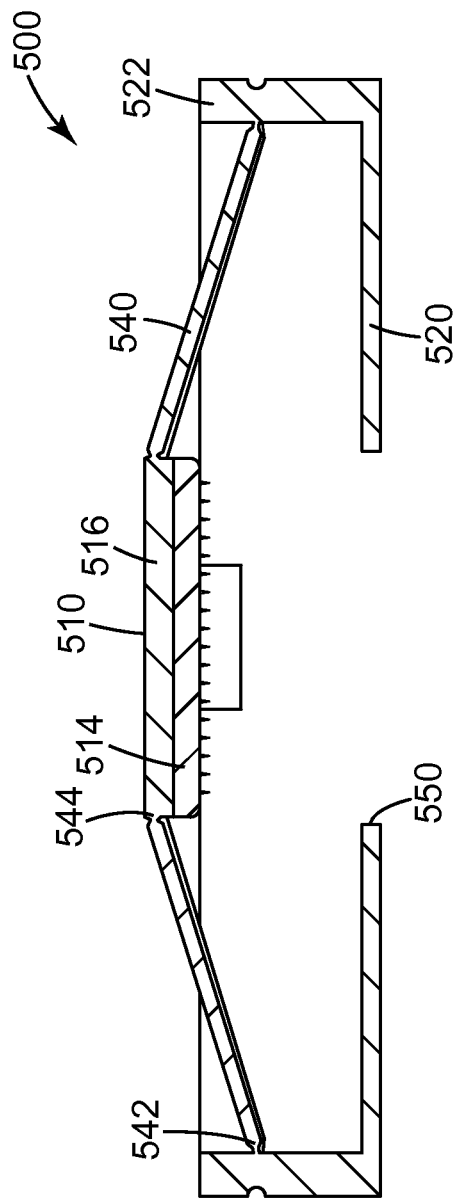
FIG. 17 is a schematic cross-section of a device in a first equilibrium position showing an aperture in the base.

In some cases the force of the application method may cause the skin to dome or protrude through the opening underneath the applicator, potentially causing a variety of effects, including the skin coming into contact with the array prior to the application, the skin being an unequal distance from the array or the actuation occurring in an uneven manner or direction or with an uneven velocity. In order to avoid premature contact of the needles with the skin, the needles could be recessed further away from the skin contacting surface. Another approach is a cross-bar or other grid arrangement at the base of the applicator to help reduce skin doming. Two cross-bars are shown in a criss-cross pattern in FIG. 13, however, one or three or more cross-bars may also be used. FIG. 13 comprises an outer ring 522 to which connecting members 540 are affixed. Also attached to the outer ring 522 are two cross bars 560 on the skin facing side of the device 100. The cross-bars 560 can either be integrally formed or separate components. In other embodiments, the opening in the base can be modified. FIG. 17 shows a cross-sectional view of a device similar to FIG. 14 wherein the connecting members 540 are affixed directly to an outer ring 522. This embodiment shows an aperture 550 in the base 520 that can be a variety of sizes. It may be of a size small enough to just allow the diameter of the array 514 and any necessary portion of the connecting member 540 to fit through on application, or be of a size that is equal to the diameter of the inner surface of the outer ring 522.

Figure 6:
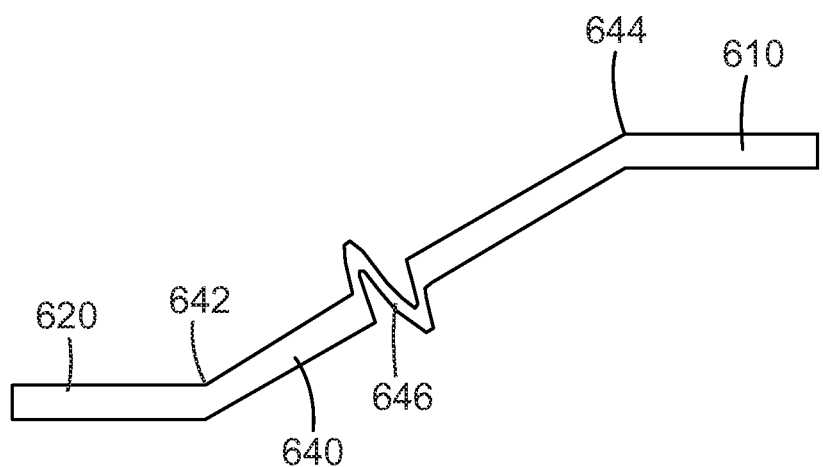
FIG. 6 is a schematic cross-sectional view of a connecting member.
Figure 7:
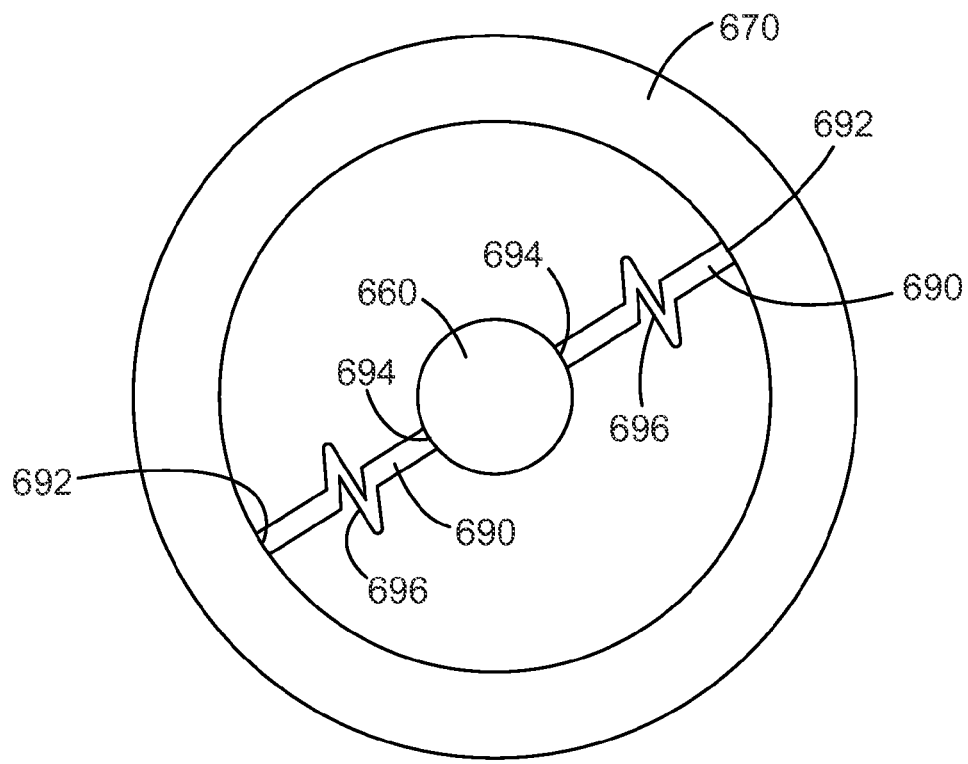
FIG. 7 is a schematic top view of another embodiment of a connecting member
Figure 8:
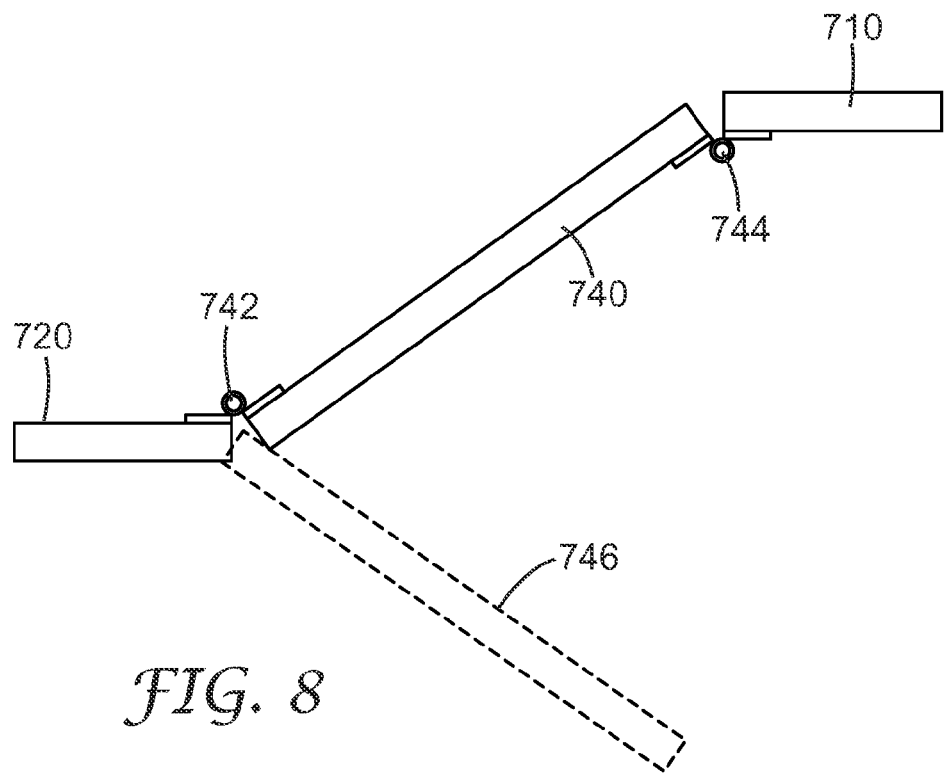
FIG. 8 is a schematic cross-sectional detailed view of one embodiment of a hinged connecting member.

The connecting member(s) will typically have some flexibility, so as to allow the device to move from the first to the second equilibrium position. It should be appreciated that the connecting member(s) is in an extended position in both equilibrium positions, as the distance between the base and array component is at a maximum. As the array passes between first and second equilibrium positions, however, the distance between base and array component is generally reduced. The force required to move the array from a first equilibrium position to a second equilibrium position may be modified through a variety of means including the shape of the connecting members or the rigidity of the connecting members, the selection of the hinge type or by adjusting the relative rigidity of the base and/or outer ring through a variety of means including material selection or thickness of the material. In particular, if the array remains substantially parallel to the skin-contacting surface, then the distance between base and array will reach a minimum at a so-called 'neutral' plane where the array component, connecting member(s), and base are substantially co-planar. If the base is fixed in space, is relatively rigid and inflexible and the array component is relatively rigid and inflexible, then the connecting member(s) must be either compressed or flexed to accommodate the reduction in distance between base and array component. In one embodiment, the connecting member is made of a thin, flexible material that may form a bow or arch as the device moves from first to second equilibrium position. FIG. 6 shows a connecting member 640 affixed to a base 620 through a first hinge 642 and affixed to an array component 610 through a second hinge 644. Connecting member 640 has an S-shaped curved section 646 which can aid in flexure and/or compression of the connecting member 640. It may be desirable to have one or more non-linear sections in the connecting member having any of a variety of shapes, such as an S-shape (shown in FIG. 6), a V-shape, a double S-shape, a W-shape, or any other suitable shape that allows for increased flexibility of the connecting member. Another embodiment of a device (shown in FIG. 7) has two connecting members 690 affixed to a base 670 through first hinges 692 and affixed to an array component 660 through second hinges 694. Connecting members 690 each have an S-shaped curved section 696 which can aid in flexure and/or compression of the connecting member 690. In one embodiment, the connecting member(s) 740 connects to the base 720 through a first hinge 742 and to the array component 710 through a second hinge 744. As shown in FIG. 8, the hinges 742, 744 are separate components that operate on the same principles as a common door hinge. The orientation 746 of the connecting member 740 in its second equilibrium position is shown by dashed lines.

Figure 9:
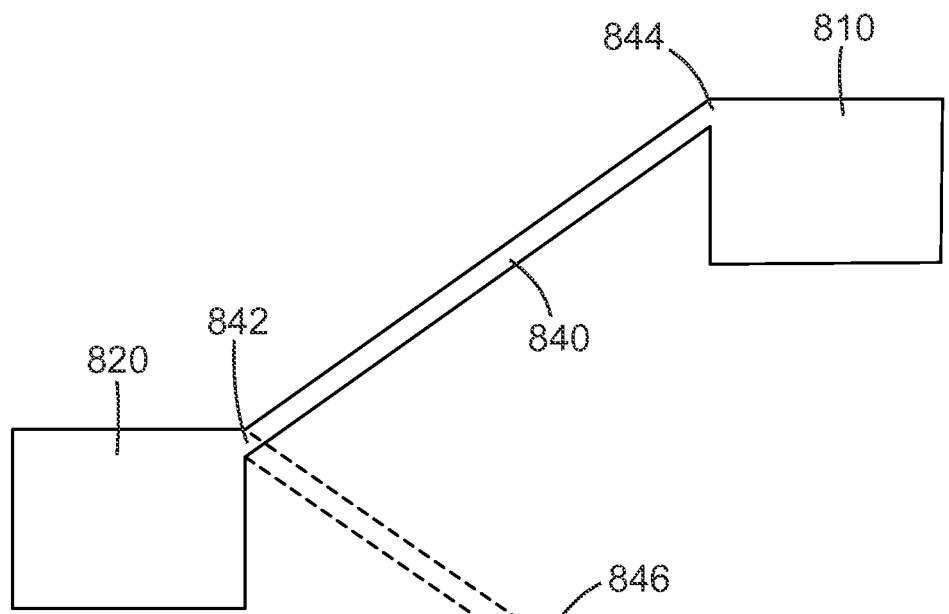
FIG. 9 is a schematic cross-sectional detailed view of another embodiment of a hinged connecting member.

In another embodiment, shown in FIG. 9, the hinges 842, 844 may be inherently formed by the joint between a relatively thin connecting member 840 and relatively thick base 820 and array component 810. The orientation 846 of the connecting member 840 in its second equilibrium position is shown by dashed lines.

Figure 10:
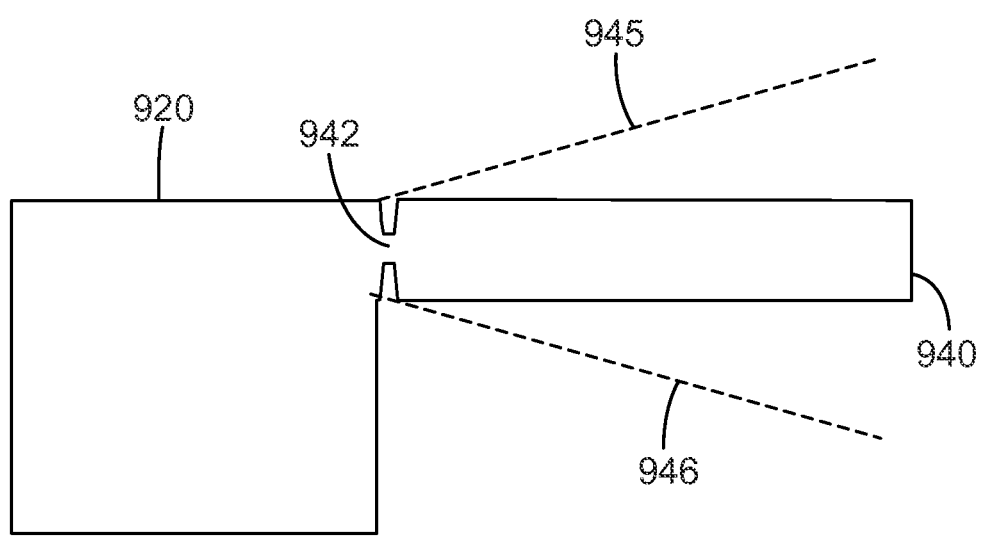
FIG. 10 is a schematic cross-sectional detailed view of still another embodiment of a hinged connecting member.
Figure 11A:
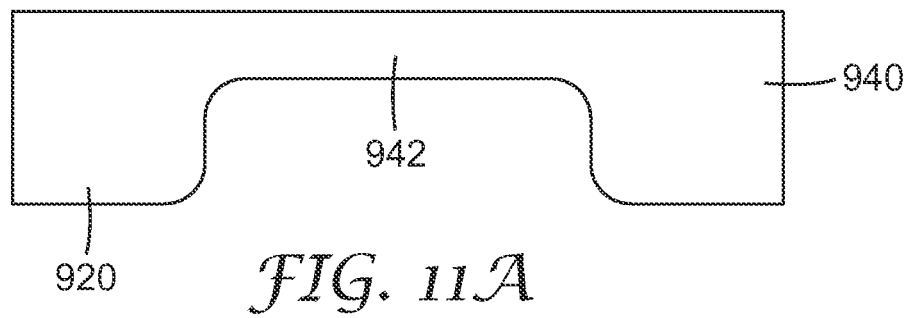
FIG. 11A-C are schematic cross-sectional detailed views of other hinge embodiments.
Figure 11B:
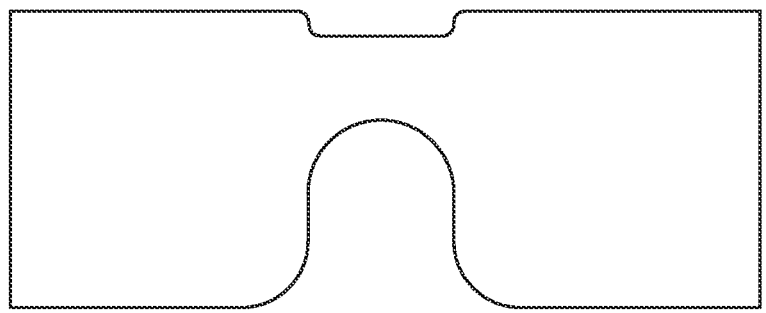
Figure 11C:
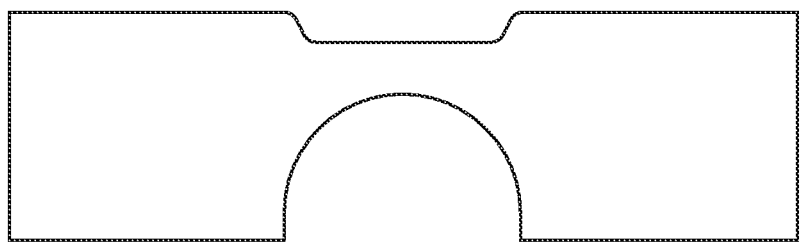

In still another embodiment, shown in FIG. 10, a hinge 942 may be constructed as an integral piece of the connection between a connecting member and the base 920 or array component (not shown). Such hinges are often called living hinges. The hinge 942 is a narrow portion connecting base 920 and connecting member 940 and is shown in a position intermediate between the first and second equilibrium positions. The orientation of the connecting member 940 in the first and second equilibrium positions 945, 946 is shown by dashed lines. Detailed view of other embodiments of living hinges are shown in FIGS. 11A-C.

Figure 12A:
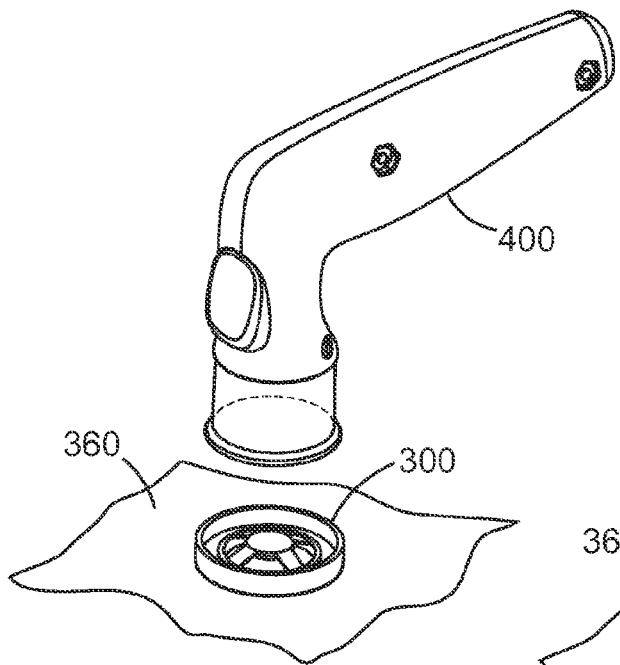
FIG. 12A-D is a perspective view of a mechanical applicator being used to apply a microneedle array to a skin surface.
Figure 12B:
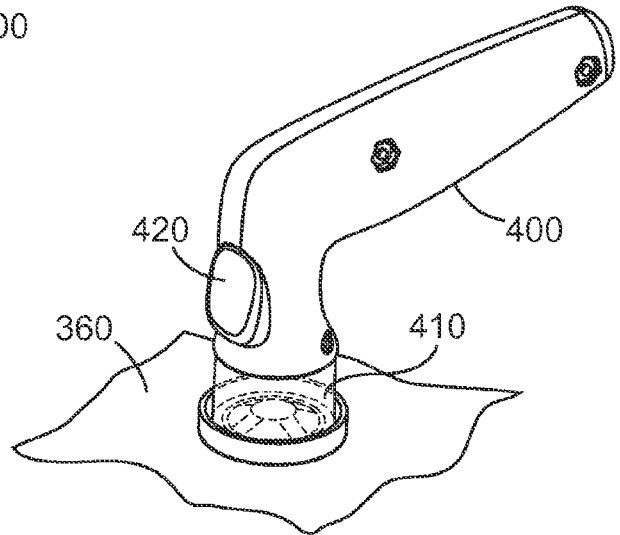
Figure 12C:
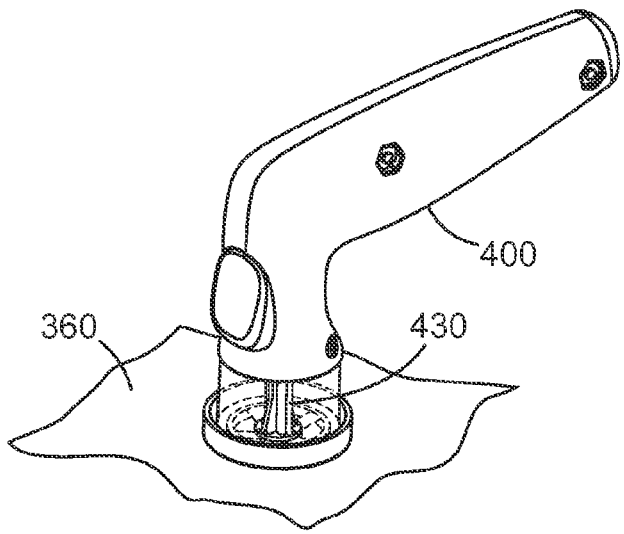
Figure 12D:
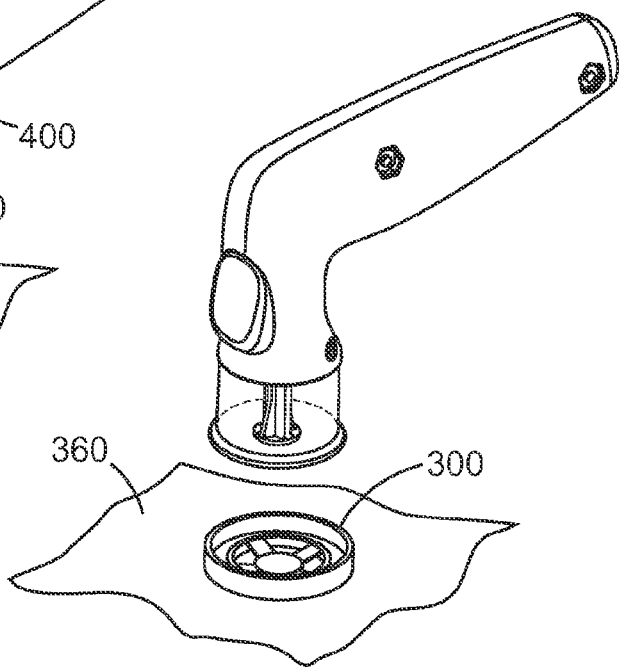

The device may be placed and/or pressed against the skin manually or with the aid of a separate application device. In one embodiment, a device having a pressure-sensitive skin adhesive on the skin facing side of the device may be manually placed and adhered onto a skin surface. The microneedle array will be in the first, recessed position when placed on the skin. The array may then be moved from the first to the second equilibrium position manually, such as by thumb or finger pressure. Alternatively, a separate applicator 400 as shown in FIGS. 12A-D may be positioned over the device 300 and activated so as to press the microneedle array into the skin 360. As shown, the device 300 is initially placed against the skin 360 in FIG. 12A. The applicator 400 is then brought into contact with the device 300 and positioned with the aid of cylindrical outer housing 410 of the applicator 400 as shown in FIG. 12B. The cylindrical outer housing 410 serves as an alignment structure to ensure that the spring-loaded piston 430 will press against the center of the device. Any other suitable alignment structures, such as one or more pins or shafts that can mate with corresponding holes or slots on the device 300, may be employed to ensure proper alignment of the piston 430 with respect to the device 300. A button 420 is pressed to release a spring-loaded piston 430 that presses the device 300 from the first to second equilibrium position so as to press the microneedle array into the skin surface 360 as shown in FIG. 12C. The applicator 400 may then be removed from the device 300, as shown in FIG. 12D, thus leaving the deployed device 300 in place on the skin surface 360. In another embodiment (not shown), the device may be releasably affixed to the applicator and both placed and pressed against the skin with the use of the applicator. The applicator may then be removed from the device leaving the deployed device in place on the skin surface as in FIG. 12D, or alternatively, the applicator may be used to remove the device immediately after the device is pressed into the skin. Where the device is removed immediately after application, it is desirable that the base be a non-adhesive surface.

In another embodiment, the present invention is a method of applying a microneedle array to a skin surface. A device is provided having a first equilibrium position wherein a microneedle array is in a recessed position within the device. The device is placed on a skin surface. A mechanical applicator is then brought into contact with the device and a drive mechanism of the mechanical applicator is aligned with the microneedle array. Force is applied via the drive mechanism to the microneedle array sufficient to move the microneedle array into contact with the skin surface. The mechanical applicator is then removed from contact with the device.

In one embodiment, an applicator may be used to allow the device to contact the skin with a desired velocity that is effective to pierce the microneedles into the skin. The desired velocity is preferably controlled to limit or prevent stimulation of the underlying nerve tissue. The maximum velocity achieved by the microneedle device upon impact with the skin is often 20 meters per second (m/s) or less, potentially 15 m/s or less, and possibly 10 m/s or less. In some instances, the maximum velocity is 8 m/s or less. In other instances, the minimum velocity achieved by the microneedle device upon impact with the skin is often 2 m/s or more, potentially 4 m/s or more, and possibly 6 m/s or more. Suitable applicators may include various types of driving mechanisms, including a spring-loaded piston, such as those disclosed in United States Patent Application Publication Nos. 2002/0091357 (Trautman et al.), 2002/0087182 (Trautman et al.), and International Publication No. WO 2005/123173 (Frederickson et al.) or a swinging member, such as disclosed in co-pending U.S. Patent Application Ser. No. 60/694447, filed Jun. 27, 2005, the disclosures of which are herein incorporated by reference.

The base, connecting member(s), hinge(s), and backing plate of the array component may be constructed of any suitable material, including metal, polymer, or ceramic, but is preferably polymer. Exemplary polymers include acrylonitrile-butadiene-styrene (ABS) polymers, polyphenyl sulfides, polycarbonates, polypropylenes, polyethylenes, acetals, acrylics, polyetherimides, polybutylene terephthalates, polyethylene terephthalates, and blends and co-polymers thereof. Polyethylenes, polypropylenes, and polycarbonate are preferred polymers.

The microneedle array may be constructed of any suitable material, including metal, polymer, or ceramic. Examples of metallic microneedle arrays include those disclosed in United States Patent Application Publication Nos. 2002/0128599 (Trautman et al.), 2002/0193729 (Cormier et al.), and 2002/0177839, the disclosures of which are herein incorporated by reference. Examples of ceramic microneedle arrays include those disclosed in United States Patent Application Publication Nos. 2002/0138049 (Allen et al.) and 2002/0082543 (Park et al.), the disclosures of which are herein incorporated by reference. The microneedle array may be constructed of a wide variety of polymeric materials. In one embodiment, the material is selected so that it is capable of forming relatively rigid and tough microneedles that resist bending or breaking when applied to a skin surface. In one aspect, the polymeric material has a melt-flow index greater than about 5 g/10 minutes when measured by ASTM D1238 at conditions of 300° C. and 1.2 kg weight. The melt-flow index is often greater than or equal to about 10 g/10 minutes and sometimes greater than or equal to about 20 g/10 minutes. In another embodiment, the tensile elongation at break as measured by ASTM D638 (2.0 in/minute) is greater than about 100 percent. In still another embodiment, the impact strength as measured by ASTM D256, "Notched Izod", (73° F.) is greater than about 5 ft-lb/inches. Examples of suitable materials include polycarbonate, polyetherimide, polyethylene terephthalate, and mixtures thereof. In one embodiment the material is polycarbonate.

In one embodiment, the base, connecting member(s), and hinge(s) may be made as a single, integrally molded piece. In another embodiment, the base, connecting member(s), hinge(s), and backing plate may be made as a single, integrally molded piece. The microneedle array may be affixed to the backing plate, for example, with the aid of an optional adhesive layer or by directly welding the array to the backing plate. In still another embodiment, the base, connecting member(s), hinge(s), backing plate, and microneedle array may be made as a single, integrally molded piece. In all of the foregoing embodiments, a single, integrally molded piece may be made using a single polymeric material for the entire piece. Alternatively, dissimilar materials may be used to form different portions of the single, integrally molded piece, for example, with the use of two-shot molding processes. In one embodiment, the base, connecting member(s), hinge(s), and backing plate will be made from a single material type, such as polyethylene or polypropylene and the microneedle array will be made of a different material type, such as polycarbonate. Such a construction may allow for the desired toughness of the microneedles while employing relatively inexpensive polymeric material for the remainder of the device. Examples of suitable molding methods are disclosed in International Publication No. WO 05/82596 (Boone et al.) and co-pending U.S. Patent Application Ser. No. 60/634,319, filed Dec. 7, 2004.

Any suitable pressure-sensitive skin adhesive may be used to allow the device to be affixed to a skin surface. As shown in FIG. 2, the pressure-sensitive skin adhesive 130 is a continuous layer on the base 120 of the device, but the pressure sensitive adhesive may be present in any of a variety of patterns and only partially cover the surface of the base 120. For example, the adhesive layer may be patterned or non-patterned, and may be continuous or discontinuous. The adhesive layer may additionally be interrupted by spaces, gaps or other structures. Typical pressure-sensitive skin adhesives include acrylates, polyisobutylenes, synthetic rubber, silicones, and blends thereof.

The microneedle arrays prepared by methods of the present invention may comprise any of a variety of configurations, such as those described in the following patents and patent applications, the disclosures of which are herein incorporated by reference. One embodiment for the microneedle devices comprises the structures disclosed in U.S. Patent Application Publication No. 2003/0045837. The disclosed microstructures in the aforementioned patent application are in the form of microneedles having tapered structures that include at least one channel formed in the outside surface of each microneedle. The microneedles may have bases that are elongated in one direction. The channels in microneedles with elongated bases may extend from one of the ends of the elongated bases towards the tips of the microneedles. The channels formed along the sides of the microneedles may optionally be terminated short of the tips of the microneedles. The microneedle arrays may also include conduit structures formed on the surface of the substrate on which the microneedle array is located. The channels in the microneedles may be in fluid communication with the conduit structures. Another embodiment for the microneedle devices comprises the structures disclosed in U.S. Patent Application Publication No. 2005/0261631 which describes microneedles having a truncated tapered shape and a controlled aspect ratio. Still another embodiment for the microneedle arrays comprises the structures disclosed in U.S. Pat. No. 6,312,612 (Sherman, et al.) which describes tapered structures having a hollow central channel. Still another embodiment for the microneedle arrays comprises the structures disclosed in U.S. Pat. No. 6,379,324 (Gartstein, et al.) which describes hollow microneedles having at least one longitudinal blade at the top surface of tip of the microneedle and solid, "star-shaped" microneedles having multiple bladed edges.

The microneedles are typically less than 500 microns in height, and sometimes less than 300 microns in height. The microneedles are typically more than 20 microns in height, often more than 50 microns in height, and sometimes more than 125 microns in height. The height of the microneedles may be measured as the distance that they protrude from a flat base or substrate. In one embodiment, the microneedles may protrude from an irregular substrate, for example, each microneedle may rest upon a flat base or pedestal that itself protrudes from a planar substrate.

Microneedle devices suitable for use in the present invention may be used to deliver drugs (including any pharmacological agent or agents) through the skin in a variation on transdermal delivery, or to the skin for intradermal or topical treatment, such as vaccination.

Microneedle devices of the present invention may be useful when applied to the skin as a "pretreatment" step, that is, when applied to the skin to disrupt the stratum corneum layer of skin and then removed. The disrupted area of skin may then be useful for allowing enhanced delivery of a solution or patch containing a pharmacological agent that is applied to the disrupted area. Microneedle devices of the present invention may also be useful when provided with a dried coating comprising a pharmacological agent that dissolves from the microneedles after they are inserted into the skin. Microneedle devices of the present invention may also be useful when provided with a fluid reservoir of pharmacological agent that can pass through one or more conduits in the device to be delivered into the skin after the microneedles are inserted into the skin.

In one aspect, drugs that are of a large molecular weight may be delivered transdermally. Increasing molecular weight of a drug typically causes a decrease in unassisted transdermal delivery. Microneedle devices suitable for use in the present invention have utility for the delivery of large molecules that are ordinarily difficult to deliver by passive transdermal delivery. Examples of such large molecules include proteins, peptides, nucleotide sequences, monoclonal antibodies, DNA vaccines, polysaccharides, such as heparin, and antibiotics, such as ceftriaxone.

In another aspect, microneedle devices suitable for use in the present invention may have utility for enhancing or allowing transdermal delivery of small molecules that are otherwise difficult or impossible to deliver by passive transdermal delivery. Examples of such molecules include salt forms; ionic molecules, such as bisphosphonates, preferably sodium alendronate or pamedronate; and molecules with physicochemical properties that are not conducive to passive transdermal delivery.

In another aspect, microneedle devices suitable for use in the present invention may have utility for enhancing delivery of molecules to the skin, such as in dermatological treatments, vaccine delivery, or in enhancing immune response of vaccine adjuvants. In one aspect, the drug may be applied to the skin (e.g., in the form of a solution that is swabbed on the skin surface or as a cream that is rubbed into the skin surface) prior to applying the microneedle device.

Microneedle devices may be used for immediate delivery, that is where they are applied and immediately removed from the application site, or they may be left in place for an extended time, which may range from a few minutes to as long as 1 week. In one aspect, an extended time of delivery may from 1 to 30 minutes to allow for more complete delivery of a drug than can be obtained upon application and immediate removal. In another aspect, an extended time of delivery may be from 4 hours to 1 week to provide for a sustained release of drug.

The present invention has been described with reference to several embodiments thereof. The foregoing detailed description and examples have been provided for clarity of understanding only, and no unnecessary limitations are to be understood therefrom. It will be apparent to those skilled in the art that many changes can be made to the described embodiments without departing from the spirit and scope of the invention. Thus, the scope of the invention should not be limited to the exact details of the compositions and structures described herein, but rather by the language of the claims that follow.

We claim:

1. A device for applying a microneedle array to a skin surface comprising:
   a base defining a skin contacting plane;
   an array component having a skin facing side comprising a microneedle array;
   a plurality of connecting members, each connecting member having a first portion affixed through a first hinge to the base and a second portion affixed to the array component through a second hinge;
   wherein the connecting member has a first equilibrium position with the microneedle array in a recessed position within the device;
   wherein the connecting member has a second equilibrium position with the microneedle array positioned so that at least a portion of the microneedle array penetrates a skin surface after removal of pressure that moves the connecting member from the first equilibrium position to the second equilibrium position;
   wherein in the second equilibrium position, the second hinge is closer to the skin contacting plane than the first hinge; and
   wherein the device comprises at least one of the following:
      (i) the connecting member comprises one or more non-linear sections,
      (ii) the cross-sectional thickness of the base is larger than the cross-sectional thickness of the connecting member, or
      (iii) the first hinge is selected from the group consisting of (a) a separate hinge component and (b) a living hinge.

2. A device as claimed in claim 1, wherein the device has four connecting members.

3. A device as claimed in claim 1, wherein the base comprises a pressure-sensitive skin adhesive disposed along the skin-contacting plane.

4. A device as claimed in claim 1, wherein the microneedle array is substantially parallel to the skin contacting plane in both the first equilibrium position and the second equilibrium position.

5. A device as claimed in claim 4, wherein the microneedle array remains substantially parallel to the skin contacting plane when moving from the first equilibrium position to the second equilibrium position.

6. A device as claimed in claim 1, wherein at least one connecting member, at least one hinge, and the base are integrally formed.

7. A device as claimed in claim 1, wherein at least one connecting member, at least one hinge, the base, and the array component are integrally formed.

8. A device as claimed in claim 1, wherein the array component and at least one connecting member are formed of dissimilar materials.

9. A device as claimed in claim 1, wherein the device is in the first equilibrium position and further comprises a covering member releasably affixed to the base.

10. A device as claimed in claim 1, wherein the microneedle array comprises a plurality of microneedles with a height of less than about 500 microns.

11. A device as claimed in claim 1, wherein the array component comprises a backing plate and a microneedle array.

12. A device as claimed in claim 11 wherein the microneedle array is releasably attached to the backing plate.

13. A device as claimed in claim 1, wherein the microneedle array further comprises a dried coating on at least a portion of the microneedle surfaces.

14. A device as claimed in claim 13, wherein the dried coating comprises a drug.

15. A device as claimed in claim 13, wherein the dried coating comprises a vaccine.

16. A device as claimed in claim 1, wherein in the first equilibrium position, the second hinge is farther from the skin contacting plane than the first hinge.

17. A device as claimed in claim 16, wherein in the first equilibrium position, the microneedle array is between the first hinge and the second hinge, with respect to the skin contacting plane.

18. A device as claimed in claim 1, wherein in the first equilibrium position, at the first hinge, the connecting member and the base form an obtuse angle on a skin facing side.

19. A device as claimed in claim 1, wherein the pressure that moves the connecting member from the first equilibrium position to the second equilibrium position moves the connecting member relative to the array component.

20. A method of applying a microneedle array to a skin surface comprising the steps of:
   providing a device a base defining a skin contacting plane;
   an array component having a skin facing side comprising a microneedle array;
   a plurality of connecting members, each connecting member having a first portion affixed through a first hinge to the base and a second portion affixed to the array component; through a second hinge;
   wherein the connecting member has a first equilibrium position with the microneedle array in a recessed position within the device;
   wherein the connecting member has a second equilibrium position with the microneedle array positioned so that at least a portion of the microneedle array penetrates a skin surface after removal of pressure that moves the connecting member from the first equilibrium position to the second equilibrium position;
   wherein in the second equilibrium position, the second hinge is closer to the skin contacting plane than the first hinge;
   wherein the device comprises at least one of the following:
   (i) the connecting member comprises one or more non-linear sections,
   (ii) the cross-sectional thickness of the base is larger than the cross-sectional thickness of the connecting member, or
   (iii) the first hinge is selected from the group consisting of (a) a separate hinge component and (b) a living hinge;
   placing the device on a skin surface; and
   applying a force to the array component sufficient to move the plurality of connecting members to the second equilibrium position.

21. A method as claimed in claim 20, wherein the force is applied using a mechanical applicator.

* * * * *

UNITED STATES PATENT AND TRADEMARK OFFICE
CERTIFICATE OF CORRECTION

PATENT NO. : 9,119,945 B2
APPLICATION NO. : 12/296590
DATED : September 1, 2015
INVENTOR(S) : John Simons et al.

Page 1 of 1

It is certified that error appears in the above-identified patent and that said Letters Patent is hereby corrected as shown below:

Specification

<u>Column 2</u>
Line 43, Delete "member" and insert -- member. --, therefor.

<u>Column 10</u>
Line 4, Delete "pamedronate;" and insert -- pamidronate; --, therefor.

Claims

<u>Column 12</u>
Line 16, In Claim 20, delete "component;" and insert -- component --, therefor.

Signed and Sealed this
Twenty-second Day of March, 2016

Michelle K. Lee
*Director of the United States Patent and Trademark Office*